US005968979A

United States Patent [19]

Brusilow

[11] Patent Number: 5,968,979

[45] Date of Patent: Oct. 19, 1999

[54] TRIGLYCERIDES AND ETHYL ESTERS OF PHENYLALKANOIC ACID AND PHENYLALKENOIC ACID USEFUL IN TREATMENT OF VARIOUS DISORDERS

[75] Inventor: Saul W. Brusilow, Baltimore, Md.

[73] Assignee: Brusilow Enterprises LLC, Baltimore, Md.

[21] Appl. No.: 09/006,432

[22] Filed: Jan. 13, 1998

Related U.S. Application Data

[63] Continuation of application No. 08/384,935, Feb. 7, 1995, abandoned.

[51] Int. Cl.[6] .......................... A01N 37/10; A61K 31/235

[52] U.S. Cl. .......................... 514/533; 514/532; 514/547; 514/549; 514/552; 514/558; 514/814; 514/815; 514/885; 554/227; 554/220; 554/218; 554/219; 560/8; 560/76

[58] Field of Search .................................... 554/227, 220, 554/218, 219; 560/8, 76; 514/532, 547, 549, 552, 558, 814, 815, 885

[56] References Cited

FOREIGN PATENT DOCUMENTS 94-22494 10/1994 WIPO ............................ A61K 49/02

OTHER PUBLICATIONS

Georges Darzens et al.: "Préparation de quelques glycérides phénylaliphatiques et leur réduction en alcools . . .", Comptes Rendus Hebdomadaires Des Seances De L'academie Des Sciences., vol. 205, Oct. 18, 1937, pp. 682–684.

Walsh et al., Chemical Abstract vol. 112, No. 231744.

Chemical Abstract, vol. 116, No. 46308, Seiki et al, "Homogenous Pharmaceutical Emulsions Containing Nonsteriodal Analogesics and Inflammation Inhibitors".

Walsh et al., The Journal of Biological Chemistry, vol. 265, No. 8, pp. 4374–4381 (1990), sn–1,2–Diacylgylcerol Kinase of *Escherichia coli*.

Newmark et al., "Butyrate and Phenylacetate as Differentiating Agents: Practical Problems and Opportunities", Jour. of Cell. Biochem., Supplement 22: 247–253(1995).

Chen et al., "Tributyrin: A Prodrug of Butyric Acid for Potential Clinical Applicaitn in Differentiation Therapy", Cancer Res., 54:3494–3499(1994).

Lea et al., "Butyramide and Monobutyrin: Growth Inhibitory and Differentiating Agents", Anticancer Res., 13: 145–150 (1993).

Acdémie Des Sciences., Chimie Organique, "Préparation de quelques glycérides phénylaliphatiques et leur réduction en alcools . . . ", pp. 682–684.

Brusilow et al., Metabolism, vol. 42, No. 10 Oct., 1993, pp. 1336–1339, "Restoration of Nitrogen Homeostasis in a Man with Ornithine Transcarbamylase Deficiency".

Maestri et al., "Prospective treatment of urea cycle disorders", pp. 923–928.

*Primary Examiner*—Gary Geist
*Assistant Examiner*—Deborah D Carr
*Attorney, Agent, or Firm*—Nikaido Marmelstein Murray & Oram LLP

[57] ABSTRACT

Two new forms of prodrug for phenylacetate, of even congeners of phenylalkanoic acid and phenylalkenoic acids, which are the phenylalkanoic or phenylalkenoic esters of glycerol, or the ethyl esters of phenylalkanoic acid or phenylalkenoic acids. These forms of the drugs provide a convenient dosage form of the drugs. The prodrugs of the invention are useful to treat patients with diseases of nitrogen accumulation, patients with certain β-hemoglobinopathies, anemia, and cancer.

10 Claims, No Drawings

TRIGLYCERIDES AND ETHYL ESTERS OF PHENYLALKANOIC ACID AND PHENYLALKENOIC ACID USEFUL IN TREATMENT OF VARIOUS DISORDERS

CROSS REFERENCE TO RELATED APPLICATION

This application is a continuation of Ser. No. 08/384,935, filed Feb. 7, 1995, now abandoned.

BACKGROUND OF THE INVENTION

The present invention relates to compounds, pharmaceutical compositions, and methods for treating several conditions with prodrugs for phenylacetate as therapeutic agents.

FIELD OF THE INVENTION

Phenylalkanoic acids are known therapeutic agents for a variety of disorders. Phenylacetate is used for the treatment of nitrogen metabolism disorders, beta-hemoglobinopathies, anemia and cancer. Various phenylalkenoic acids can be used in the treatment of the same disorders. The prodrugs disclosed in the present invention are useful therapeutic agents for a number of disorders, and possess some advantages over the forms of the drugs administered in the prior art.

Nitrogen Metabolism Disorders

In a healthy person, the potentially toxic nitrogenous compounds which accumulate as the body degrades proteins are synthesized into urea which is rapidly excreted into the urine. However, for those who suffer kidney failure, liver failure or inborn errors of urea synthesis, this pathway is defective. The accumulation of nitrogenous compounds resulting from such a blockage leads to considerable morbidity and mortality.

In the case of an inborn error of urea synthesis, the major metabolic abnormality is the inability of the body to convert waste nitrogen into urea. As a consequence, various nitrogenous metabolites accumulate in the body, the most toxic being ammonium, although other materials, such as glutamine and alanine also increase.

Previous therapeutic approaches for treating patients with urea cycle enzymopathies (as well as other nitrogen accumulation diseases cited earlier) have been designed to reduce the requirement for urea synthesis by quantitative and qualitative manipulation of dietary protein, amino acids and/or their nitrogen free analogues. Generally speaking, however, the mortality of inborn errors of the urea-cycle remained high and success was measured in terms of increased survival time. Thus, for example, even with the above-cited therapeutic approaches, children with the neonatal form of these diseases rarely survive past one year of age (Maestri, et al., *The Journal of Pediatrics*, Vol. 119, No. 6, 923–928 (1991)).

DESCRIPTION OF RELATED ART

A more recent approach to remedy this pervasive problem is described in U.S. Pat. No. 4,284,647 to Saul W. Brusilow, wherein benzoic acid, phenylacetic acid, or the salts thereof, convert the waste nitrogen into amino acid acylation products which the body can successfully excrete as urinary nitrogen. More specifically, the patent teaches that phenylacetate reacts with the nitrogen to form phenylacetylglutamine which is subsequently excreted by the body. Since such a reaction is in no way dependent on the urea synthesis or excretion, it is an effective treatment for those suffering from nitrogen accumulation diseases. See also "Treatment of Inborn Errors of Urea Synthesis," *New England Journal of Medicine*, 306; 1387–1392 (1982).

U.S. Pat. No. 4,457,942, also to Saul W. Brusilow, discloses that even-numbered phenylalkanoic acids can be advantageously used for the treatment of nitrogen accumulation diseases.

When administered to humans, even numbered phenylalkanoic acids, such as phenylbutyrate, can be broken down by betaoxidation, two carbon atoms at a time, to eventually yield phenylacetate which, as described above, has been found useful for removing waste nitrogen from the blood stream. The administration of even numbered phenylalkanoic acids such as phenylbutyrate has the advantage that the higher molecular weight compounds do not have the offensive odor which phenylbutyrate has.

The above treatments, although effective, have a substantial disadvantage. The dose of sodium phenylbutyrate for an adult with a urea cycle disorder is 20 grams/day. This requires that the patient take forty (40) tablets of 0.5 grams each, per day. Problems of patient compliance arise when such large daily doses are required. The administration of sodium phenylbutyrate has a second disadvantage to many patients—patients who should restrict their daily dose of sodium. The above daily dose of sodium phenylbutyrate provides 2.5 gm of sodium per day, every day (it is recommended that adults consume less than 2.4 grams/day total sodium).

The substitution in therapy of phenylacetate or phenylbutyrate, by the compounds of the present invention, provides the therapeutic compound in a more convenient dosage form. In addition, the compounds of the present invention may eliminate the peaks and valleys in drug levels since the breakdown of these higher molecular weight compounds by beta-oxidation is a gradual process. In addition, the Na component of the prior art is replaced with glycerol, which is a normal product of metabolism.

Cancer

Phenylbutyrate and phenylacetate are being investigated as a treatment for various malignant diseases. The exact mechanism by which this therapy causes improvement in the patient is not entirely clear.

It has been observed that primary central nervous system tumors are reminiscent of immature brain, and the immature brain is known to be more vulnerable to damage by phenylacetate than the mature brain (as is observed in phenylketonuria). Sodium phenylacetate appears to promote the differentiation of cultured human glioblastoma cell lines with reduced expression of malignant phenotype.

Systemic treatment of rats bearing intracranial gliomas with phenylacetate resulted in significant tumor suppression with no apparent toxicity to the host. Early clinical results suggest that phenylacetate may become an important tool in the management of certain tumors in light of its demonstrated efficacy, and lack of toxicity (Samid et al., *Cancer Research*, 54, 891–895, 1994, and Cinatl et al., Cancer Letters, 70, 15–24, 1993).

A similar theory may be applied in treating prostate cancer with phenylacetate. The phenylacetate is thought to act as a differentiation inducer of leukemic and other less differentiated tumor cells, such as hormone refractory prostate cancer.

Cultured cells of androgen dependent prostate cell lines with sodium phenylacetate show inhibition of cell proliferation. In addition, such cells show reversion to non-malignant phenotype by in vivo and in vitro assessments (Samid et al., *The Journal of Clinical Investigation*, Vol. 19, 2288–2295, 1993).

Phenylacetate may exert an anti-tumor affect by another mechanism. Glutamine is the major nitrogen source for nucleic acid and protein synthesis, and substrate for energy in rapidly dividing normal and tumor cells. Compared to normal tissue, most tumors, due to decreased synthesis of glutamine along with accelerated utilization and catabolism, operate at limiting levels of glutamine availability and consequently are sensitive to further glutamine depletion. In the body, phenylacetate conjugates with glutamine, with subsequent renal excretion of phenylacetylglutamine. This pathway is the reason that phenylacetate administration is useful in the treatment of nitrogen accumulation diseases. Because phenylacetate removes glutamine, administration of phenylacetate may limit the growth rate of rapidly dividing cells such as tumor cells.

By one or more of the above mechanisms, phenylacetate causes a decrease in tumor characteristics of a variety of tumor cells. Because of its known non-toxicity, phenylacetate is a promising therapeutic agent, either alone or in combination with other anti-tumor agents.

Hemoglobinopathies

Sodium phenylbutyrate is thought to cause improvement in certain β-hemoglobinopathies because the sodium phenylbutyrate induces the expression of fetal hemoglobin. Thus the absent or aberrant β-hemoglobin is substituted with fetal hemoglobin.

Numerous agents which induce the expression of fetal hemoglobin have been used to treat sickle cell anemia and β-thalassemias. Some of the agents which increase the production of fetal hemoglobin however, have serious side effects that are not consistent with their use as long term therapeutic agents. However, sodium phenylacetate and sodium phenylbutyrate have been previously used to treat urea cycle disorders and are known to be very well tolerated and free of adverse reactions in clinical use. Preliminary clinical studies of patients with beta thalassemia indicate that treatment with sodium phenylbutyrate results in a response in many patients. The response is particularly good in patients with relatively high erythropoietin levels. Thus, combination therapy of the phenylbutyrate and erythropoietin may be effective. Hydroxyurea given orally has also been shown to increase hemoglobin levels in some thalassemia patients. Clinical studies of thalassemia patients treated with a combination of hydroxyurea and sodium phenylbutyrate has produced increased hemoglobin levels in some patients.

SUMMARY OF THE INVENTION

The compounds of the present invention, triglycerides of phenylalkanoic acids or phenylalkenoic acids, and ethyl esters of phenylalkanoic acids or phenylalkenoic acids, provide a more convenient dosage form of drugs for treatment of nitrogen accumulation disorders, cancer, anemia and hemoglobinopathies. The compounds of the invention are oils or soft fats. Where the prior art dose for an adult would have been forty 0.5 g tables/day, the present invention provides the same amount of active compound in approximately four (4) teaspoonfuls per day. The dosage form of the present invention also decreases sodium intake in patients, which is advantageous in certain patients, and may also provide the active component of the drug, the phenylalkanoic or phenylalkenoic acid, at a more constant level.

The compounds of the invention may be used for the treatment of nitrogen accumulation disorders, portal systemic encephalopathy, and diseases involving impaired hepatic function. Additionally, the use of triglycerides and/or the esters of the present invention alone or in combination with hydroxyurea and/or erythropoietin, may be used for the treatment of beta chain hemoglobinopathies. The compounds of the invention are suitable for the treatment for various leukemias and solid tumors.

The compounds of the invention can be produced by standard esterification procedures. Additionally, many of the compounds of the invention are commercially available.

DESCRIPTION OF THE PREFERRED EMBODIMENTS

The present invention utilizes compounds of the formula:

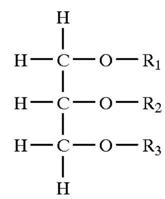

wherein $R_1$, $R_2$, and $R_3$ are independently, H,

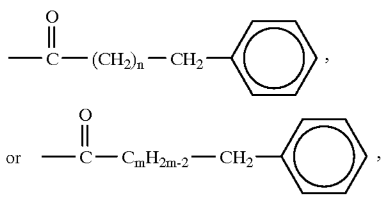

and n is zero or an even number, m is an even number and at least one of $R_1$, $R_2$, and $R_3$ is not H.

The most preferred compounds are those wherein none of $R_1$, $R_2$ and $R_3$ is H. The advantage over the prior art of decreased dosage is greater with such triglycerides.

The present invention also utilizes ethyl esters of the formula II (II)

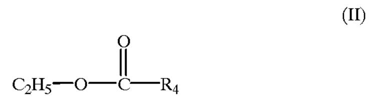

wherein $R_4$ is

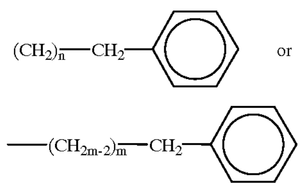

and n is zero or an even number, and m is an even number.

The compounds of the invention include compounds with substituents of even numbered congeners of phenylalkanoic and phenylalkenoic acids. Preferably the substituents contain 24 or fewer carbon atoms. Most preferably, n and m are 0, 2, 4 or 6.

The compounds of the present invention can be used separately or in the form of mixtures. The amount of the compounds of the present invention which is administered to patients for the present purposes can vary widely from case to case. Normally, however, the daily dosage for the compounds should fall in the range of 450 to 600 mg/kg body weight for children, and from 9.9 to 13 grams for adults. The size and frequency of the dosages given at any time may be varied as described provided the indicated total daily does is not significantly modified. Preferably the compounds of the invention are administered orally, although in some circumstances, administration may be other routes such as topically or parenterally.

Metabolic Fates of the Compounds of the Invention

Pancreatic lipase is able to hydrolyse the triglyceride compounds of the invention to produce glycerol and phenylalkanoic acids or phenylalkenoic acids. The glycerol is then metabolized in the usual manner.

In their experiments with dogs, Raper and Wagner (Biochem Journal 22:188 (1928)) demonstrated that phenylalkanoic acids are oxidized at the beta carbon during metabolism to cause cleavage of two carbons at a time. Thus, they found that 80% of the phenylbutyrate administered to dogs appeared in the urine as the glycine conjugate of phenylacetate. Unlike dogs, man only produces an acetylation product of glutamine from phenylacetate. Thus, when phenylbutyrate is administered to a human as either a fatty acid or a salt thereof, the phenylacetate formed as a result of beta oxidation will acetylate the glutamine thus causing the formation of phenylacetylglutamine which will be excreted by the kidney. The beta oxidation process is not limited to phenylbutyrate. In fact, any even numbered phenylalkanoate can be metabolized to phenylacetate. Thus phenylhexanoate, phenyloctanoate and phenyldecanoate are also effective to control waste nitrogen levels.

Unsaturated fatty acids are oxidized by the same general pathway as saturated fatty acids. Two additional enzymes may be used, one which can reversibly shift the double bond from cis to trans configurations, and one which hydrates the double bond to form hydroxy fatty acids. The compounds are then substrates for the beta oxidation enzymes.

The ethyl esters of formula II are thought to be metabolized by spontaneous degradation in the intestine.

It is anticipated that the toxicity of tri-glycerides of phenylbutyrate and other compounds of this invention to patients would be low when these compounds are administered to patients because the fate of such compounds is phenylbutyrate which is beta oxidized to form phenylacetate. Glycerol is also produced, but it is a normal body constituent which is either converted to glucose or oxidized. For the ethyl esters, ethanol is produced, but in such small quantities as to be non-harmful. The phenylacetate metabolic product, on the other hand, has no known toxicity and is approved for investigational use in humans (IND #17123).

We claim:

1. A method of treating a nitrogen metabolism disorder in a patient in need of such treatment, comprising administering to said patient an effective amount of a compound of formula (I)

(I)

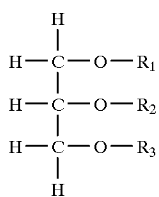

wherein $R_1$, $R_2$ and $R_3$ are independently H,

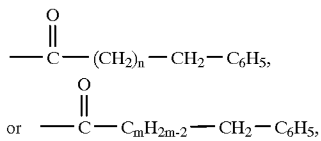

n is zero or an even number from 2–24 and m is an even number from 2–24, provided that at least one of $R_1$, $R_2$ and $R_3$ is other than H.

2. A compound of formula I (I)

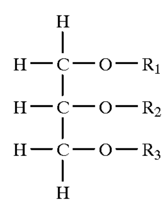

wherein $R_1$, $R_2$, and $R_3$ are independently

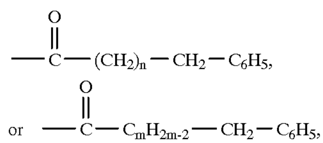

and n and m are an even number from 2 to 24.

3. A pharmaceutical composition comprising (a) a compound of formula I (I)

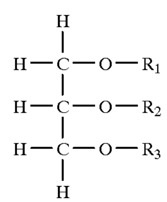

wherein $R_1$, $R_2$, and $R_3$ are independently H,

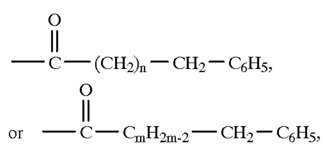

and n is zero or an even number from 2–24, m is an even number from 2–24, wherein at least one of $R_1$, $R_2$, and $R_3$ is not H, and (b) a component selected from the group consisting of hydroxyurea and erythropoietin.

4. A pharmaceutical composition suitable for the treatment of nitrogen metabolism disorders, β-hemoglobinopathies, anemia or cancer comprising a compound of formula I (I)

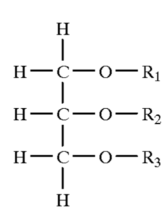

wherein $R_1$, $R_2$, and $R_3$ are independently

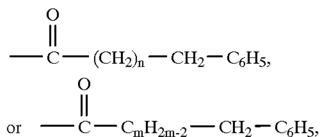

n is zero or an even number from 2–24, and m is an even number from 2–24 and a pharmaceutically acceptable excipient.

5. A pharmaceutical composition suitable for the treatment of nitrogen metabolism disorders, β-hemoglobinopathies, anemia and cancer comprising ethyl esters of the formula II

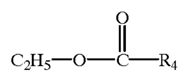

wherein $R_4$ is $C_mH_{2m-2}$—$CH_2$—$C_6H_5$ and m is an even number from 2–24, together with at least one pharmaceutically acceptable excipient.

6. A pharmaceutical composition suitable for the treatment of nitrogen metabolism disorders, β-hemoglobinopathies, anemia or cancer comprising a compound of formula I

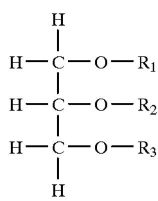

wherein $R_1$, $R_2$, and $R_3$ are independently H,

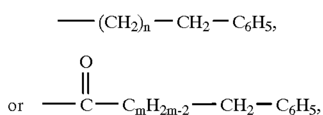

n is zero or an even number from 2–24, and m is an even number from 2–24, provided that at least one of $R_1$, $R_2$, and $R_3$ is a compound of the formula

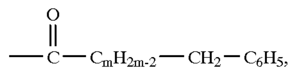

and a pharmaceutically acceptable excipient.

7. A compound of the formula I

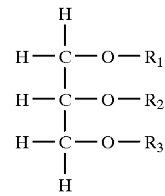

wherein $R_1$, $R_2$, and $R_3$ are independently H,

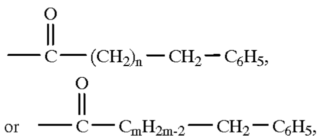

and n is zero or an even number from 2–24, and m is an even number from 2–24, with the provisos that at least one of $R_1$, $R_2$, and $R_3$ is not H, and that when n is 0 or 2, then one of $R_1$, $R_2$, and $R_3$ is a compound of the formula

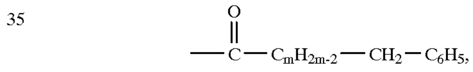

8. The compound of claim 7, wherein n is 0, 2, 4, or 6, and m is 2, 4, or 6.

9. A pharmaceutical composition suitable for the treatment of nitrogen metabolism disorders, β-hemoglobinopathies, anemia or cancer, comprising the compound of claim 7, and a pharmaceutically acceptable excipient.

10. The composition of claim 9, wherein n is 0, 2, 4, or 6, and m is 2, 4, or 6.

* * * * *